United States Patent [19]

Jules

[11] Patent Number: 5,800,475
[45] Date of Patent: Sep. 1, 1998

[54] HEARING AID INCLUDING A COCHLEAR IMPLANT

[75] Inventor: Fardeau Michel Gustave Jules, Les Milles, France

[73] Assignee: Bertin & Cie, Plaisir, France

[21] Appl. No.: 654,872

[22] Filed: May 29, 1996

[30] Foreign Application Priority Data

May 31, 1995 [FR] France ................... 95 06475

[51] Int. Cl.$^6$ ...................................... A61N 1/36
[52] U.S. Cl. ............................................ 607/57
[58] Field of Search .................. 607/55–57; 600/25; 381/68–68.3, 69.2; 395/2.2, 2.8

[56] References Cited

U.S. PATENT DOCUMENTS

| | | | |
|---|---|---|---|
| 5,388,182 | 2/1995 | Benedetto et al. | |
| 5,439,483 | 8/1995 | Duong-Van | |
| 5,597,380 | 1/1997 | McHermott et al. | 607/57 |
| 5,601,617 | 2/1997 | Loeb et al. | 607/57 |
| 5,603,726 | 2/1997 | Schulman et al. | 607/57 |

FOREIGN PATENT DOCUMENTS 2383657 10/1978 France.

OTHER PUBLICATIONS

Rioul, et al, "Wavelets and Signal Processing", IEEE Signal Processing, vol. 8, No. 4, Oct. 1991, pp. 1 and 14–38.
Loeb, "Le Remplacement des Organes Fonctionnels de L'oreille", Pour la Science, Apr. 1985, pp. 32–39.

*Primary Examiner*—Jeffrey R. Jastrzab
*Attorney, Agent, or Firm*—Watson Cole Stevens Davis, P.L.L.C.

[57] ABSTRACT

The hearing aid includes n electrodes for being implanted in the cochlea at n different points chosen to allow identification by the brain of multiple frequency bands of a sound spectrum. A microphone receives the sound spectrum and outputs a sound signal. The instantaneous energy in the frequency bands in the sound signal is measured. The electrodes are operated cyclically as a function of the energy measured in the frequency bands and in an order determined in accordance with a time distribution of the energy in the frequency bands.

14 Claims, 2 Drawing Sheets

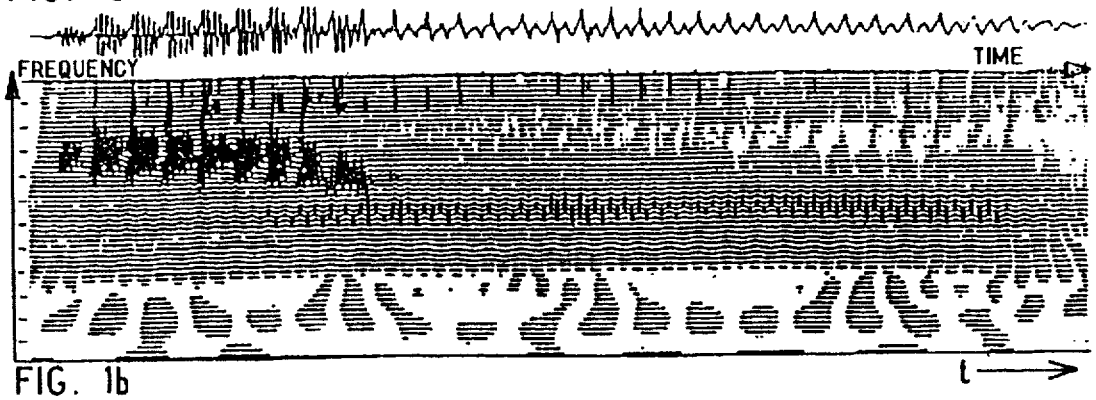
FIG. 1a
FIG. 1b
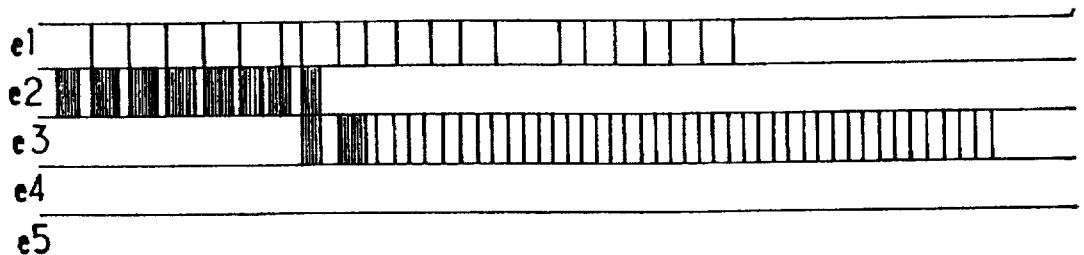
FIG. 3a
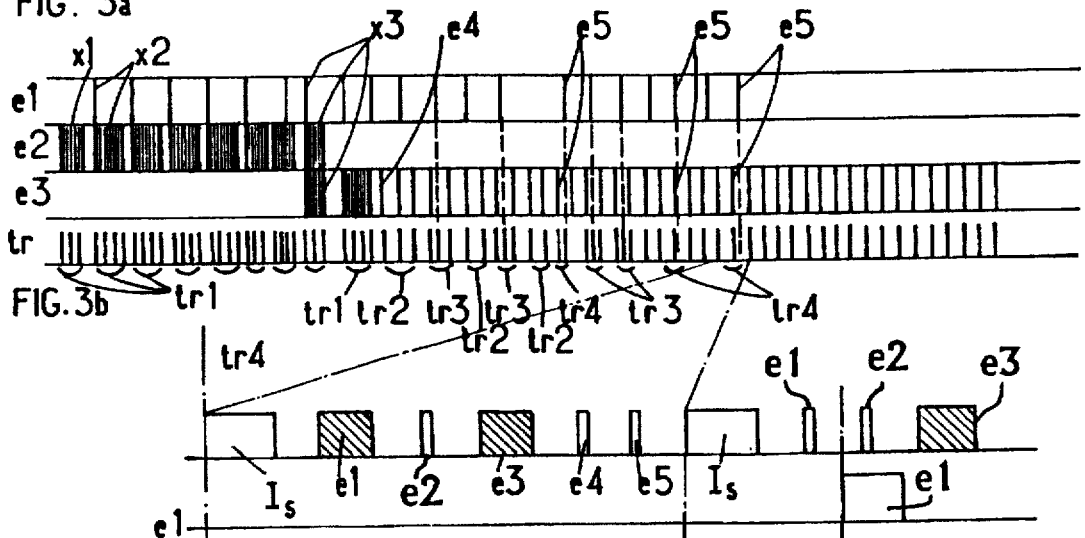
FIG. 3b
FIG. 3c
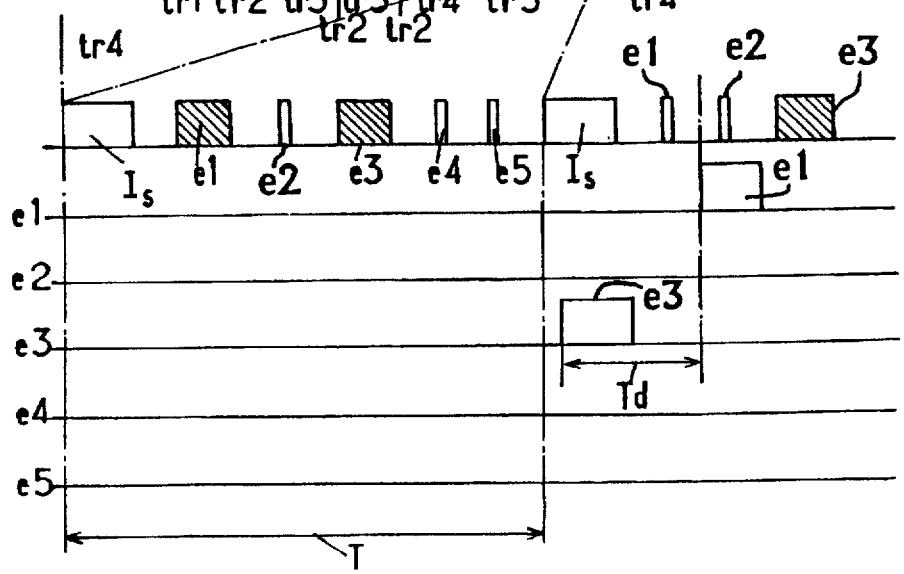

HEARING AID INCLUDING A COCHLEAR IMPLANT

FIELD OF THE INVENTION

The present invention relates to hearing aids of the type including a cochlear implant. Such hearing aids are used mainly for the rehabilitation of sensorineural deaf individuals having a large number of undamaged auditory fibers, and for this purpose they include electrodes implanted in the tympanic lip of the cochlea.

BACKGROUND OF THE INVENTION

The principles of these hearing aids have been described in particular, on the one hand, in French Patent FR 2 383 657 as regards their technical, more specifically electronic part, and on the other hand, in an article by Gerald Loeb published in the journal "Pour la Science" in April 1985, pages 32 to 39. This article mainly illustrates the problems related to the implantation of the apparatus and the difficulties encountered as regards the coupling between the auditory nerve and the electrodes responsible for communicating the useful signals to it. These two documents should therefore be referred to for further details concerning the state of the art for hearing aids of this kind.

To summarize, at the present time a hearing aid with cochlear implant may be regarded as comprising essentially an outer module communicating, generally inductively, with a module implanted in the inner ear, the outer module producing signals evidencing the surrounding sound spectrum so as to transmit them to the inner module, accompanied by any complementary signals which may be used by the inner module for its auto-power supply.

The inner module comprises a group of n electrodes (with at the present time n generally greater than or equal to eight), arranged in a bundle which is inserted into the tympanic lip by the surgeon. The inner module also comprises a circuit for operating these electrodes in bipolar mode, together with, depending on the construction, either a pair of electrodes brought simultaneously to opposite potentials, or a single electrode brought to a potential which differs from the set of other electrodes. The inner module finally comprises a circuit providing it with its own electrical power supply, as well as a sub-cutaneous inductor. It should be noted that the number of electrodes is related mainly to the room available in the tympanic lip and to the problems of crosstalk between the electrodes. It therefore depends on the technology of construction, as well as on the surgical implantation protocol.

The outer module of the hearing aid comprises, firstly, a microphone for picking up the surrounding sound spectrum and delivering a sound cue signal, a circuit for decomposing this sound cue signal into a plurality of frequency signals representative of predetermined audio frequency bands of said sound spectrum, means enabling these frequency signals to be assigned parameters relating, on the one hand, to the general physiology of the ear and, on the other hand, to the particular characteristics of the ear of the patient and of his or her implanted electrodes, and means for, on the basis of said frequency signals assigned said parameters, producing pulses which are representative of the energy contained in each of said frequency bands and are intended to be applied selectively to each of said electrodes through an inductor communicating with the inductor of the implanted module.

The electrodes are generally operated cyclically with the help of a frame signal which affords cyclic control of the electrodes to allow excitation either of one electrode at a time, or of two electrodes simultaneously.

Despite the considerable technical progress from which hearing aids have benefitted in recent years as regards miniaturization and the use of integrated circuits working with software specially adapted in particular in respect of the filtering of the sound signal, they continue to suffer from a number of technical deficiencies which make their intensive use in the treatment of profound deafness still problematic.

Indeed, firstly, a large disparity is observed in the results obtained among patients fitted with a hearing aid, from good following of a conversation without lipreading for certain patients, up to a near-absence of results for others, despite definite recovery of the sound environment.

It is known that a speech signal includes a number of elementary sounds or phonemes, as well as transient states for passing from one phoneme to another. Thus, firstly may be distinguished the "vowels" which, taken in the broad sense, designate a continuous sound produced by exciting the vocal chords and therefore embraces sounds such as for example, for the French, "ou", "é", "è" etc. The vowels in reality consist of a superposition of several frequencies called "formants" corresponding to the resonance of the various cavities of the vocal tract which are excited by the generator constituted by the vocal chords.

There are also the "consonants" which are in general classified into various categories such as the "sibilants", the "palato-alveolar fricatives", the "fricatives", etc. which may correspond to rapid and particular movements of the tongue, to rapid variations in the speaker's flow rate of air or else to variable reductions in the passage of air through the vocal tract.

A consonant is therefore characterized by a very rich and very rapidly changing spectrum of instantaneous frequencies. This change is very dependent on the preceding sound and on the succeeding sound.

Taking for example the pronunciation of the word "CHAT" by a French speaker, the consonant "CH" gives rise to a very rich frequency spectrum comparable to that of white noise or else of the ambient "whistling" of the air in a microphone, whereas the vowel "A" is represented by two relatively well-defined frequencies modulated by the fundamental frequency of the vocal chords.

It is thus understood that, owing to the extreme complexity of the instantaneous sound spectra, one of the major difficulties encountered in the design of hearing aids with cochlear implant lies in transcribing the instantaneous sound spectrum received as faithfully as possible into usable frequency signals so as to be matched to the appropriate operating of the electrodes of the implanted module of the hearing aid.

However, the solutions advocated in this respect in the prior art are unsatisfactory essentially for the following two reasons, depending on the way in which the spectral analysis is carried out.

On the one hand, the electronic filters used for the decomposition of the sound spectrum do not work rapidly enough, since they require some time to react to the input signal which enters within their passband and additionally they die out progressively as the frequency of the input signal leaves the passband of the filter. As a result, the instantaneous frequency representation which they produce is not faithful all the more so since in practice the use of a bank of filters for a cochlear implant hearing aid generally requires multiplexing of the readout from the outputs of the various filters, adding further inaccuracy to the detection of appearance of such or such a frequency.

On the other hand, in the more recent constructions which generally implement decomposition by fast Fourier transform or FFT, a limited time window is taken into account and accordingly the mean spectrum is compiled over this window, independently of the changing conditions of the spectrum of the input signal during this time window.

Signal decomposition techniques have recently been developed which use what is commonly known as the "theory of wavelets". This technique has been described in an article by O. Rioul and M. Vetterli in the journal "IEEE SP Magazine", published in the October 1991 issue, pages 14 to 38. This article demonstrates, in particular through FIG. 5.4 therein, that a sound spectrum can be decomposed into its frequency components via a "wavelet transform" with a temporal fineness which is all the greater the higher the frequency within the spectrum. This amounts to saying that the signals obtained at the output of an analysis system implementing a wavelet transform may contain not only a cue for the energy per frequency or per frequency band, but also a time cue per frequency or per frequency band.

Thus, the purpose of the invention is to propose a hearing aid of the type described above, enabling the inner ear to be supplied with a sound cue corresponding more faithfully to the instantaneous sound spectrum applied to the hearing aid and thus providing the patient equipped therewith, if not with a degree of listening comfort which best reproduces that of a normal hearer, at least with better perception of the instantaneous sound spectrum which surrounds him.

The subject of the invention is therefore a hearing aid of the type including n electrodes intended to be implanted in the cochlea respectively at n different points chosen to allow the identification by the brain of a plurality of different frequency bands of the sound spectrum received by the hearing aid, the latter comprising:

a microphone, means for measuring the instantaneous energy of the sound signal in said frequency bands, and means for cyclically operating said n electrodes as a function of the energy measured in said respective frequency bands, said hearing aid also comprising:

means for determining the time distribution within the sound signal of the energy in each of said frequency bands, and means for exciting said electrodes at each cycle in the order corresponding to said time distribution.

It follows from these characteristics that the electrodes distributed within the tympanic lip of the ear can be operated not only as a function of the energy which they are to receive, which energy is specific to the frequency band to which such or such an electrode is assigned, but also as a function of a time cue enabling their instants of excitation to be matched to the temporal phenomena contained in the sound spectrum received.

According to another characteristic of the invention, said means for determining the time relation are designed to apply a wavelet transform to said sound spectrum.

According to another characteristic of the invention, the means for exciting the electrodes are designed to produce trains of successive pulses constituting a frame (tr1 to tr4) in which the pulses are defined as a function of the energy and of the time relation.

According to another characteristic of the invention, the means for exciting the electrodes are designed to define the pulses by their duration, their frequency of recurrence and/or their relative phase.

According to another characteristic of the invention, the time relation is defined with respect to a time reference such as the start of the first pulse of each of the frames (tr1 to tr4).

According to another characteristic of the invention, the means for exciting said electrodes are designed to produce a succession of binary words in which are contained the command cues for the operating of the electrodes, for the amplitude of the pulses to be applied thereto and/or for the energy required to be contained in the pulses.

According to another characteristic of the invention, the invention further comprises, in combination with any or all of the above elements, means for assigning to the cue for the energy in the frequency bands at least one parameter evidencing the physiological behavior of the ear of a normal hearer and/or of the electrodes implanted in the inner ear of the patient.

According to another characteristic of the invention, the invention further comprises, in combination with any or all of the above elements, means for assigning to the cue for the energy in the frequency bands at least one parameter which takes the ambient noise into account.

BRIEF DESCRIPTION OF THE DRAWINGS

Other characteristics and advantages of the present invention will emerge in the course of the description which follows, given merely by way of example and undertaken with reference to the appended drawings in which:

FIGS. 1a and 1b are frequency/time charts of the sound spectrum appearing when a French speaker utters the word "ALICE";

FIGS. 3a to 3c show charts illustrating the operation of the hearing aid according to the invention as a function of time.

DESCRIPTION OF THE PREFERRED EMBODIMENT

Figure 2:
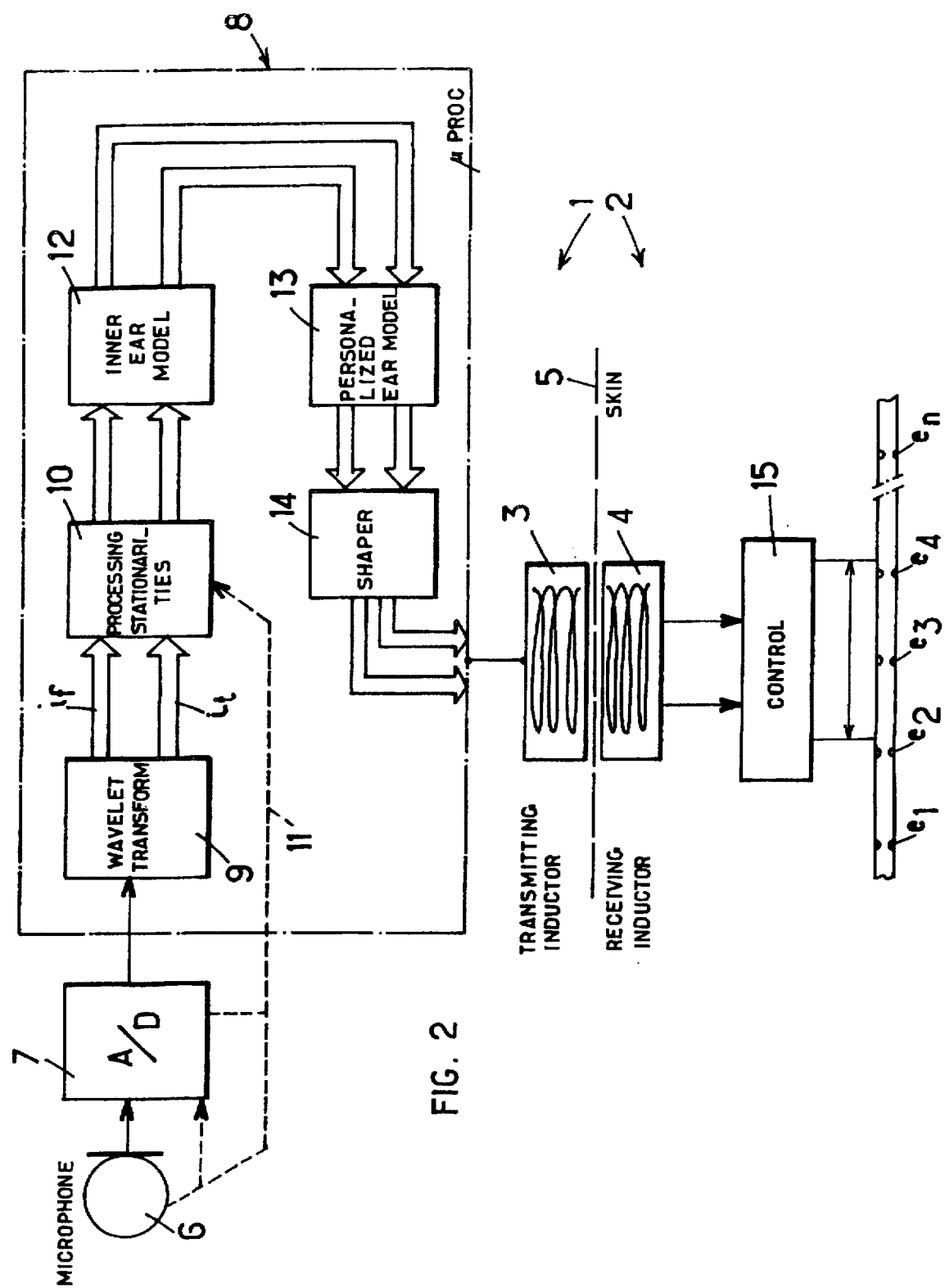
FIG. 2 is a basic diagram of a hearing aid according to the invention.

Represented in FIG. 2 is the simplified diagram of an example embodiment of a hearing aid according to the invention.

In the configuration depicted, this hearing aid comprises an outer module 1 and an inner or implantable module 2, communication between these two modules being effected via a transmitting inductor 3 located outside and via a receiving inductor 4 implanted under the skin 5 of the patient.

The outer module 1 comprises a microphone 6 worn by the patient in such a way as to be able to pick up the surrounding sound spectrum. The output of this microphone is linked to an analog/digital converter 7, this converter working, preferably, at a relatively high sampling frequency (at least of the order of 8 kHz, for example). Of course, a device for automatic or manual volume adjustment (not represented) can be provided between this microphone 6 and the converter 7.

The output of the converter 7 is linked to a microprocessor 8 of the signal processor type, for example with its peripheral integrated circuits (memories, sequencer, etc.). Through its internal program this microprocessor embodies the means which make it possible to carry out the functions which will now be described and which are represented symbolically in FIG. 2 with the help of suitable rectangles. Those skilled in the art will be able to write the appropriate program for controlling the microprocessor 8 with the help of the descriptive elements given below of these functions.

The digital signal formulated by the converter 7 is firstly subjected at 9 to means of analysis by wavelet transform according to the precepts expounded in the aforesaid article by Messrs Rioul and Vetterli. This analysis gives rise to the production of essentially two cues If and It in each examined frequency band of the sound spectrum, namely on the one hand, a frequency cue evidencing the energy content of the frequency band examined and, on the other hand, a time cue evidencing the relative temporal position of the energy cues of the frequency bands with respect to each other.

It should be noted that the means of analysis by wavelet transform use a time window of duration varying as a function of frequency and that, according to an advantageous characteristic of the invention, this analysis time window is made to move continuously in time, the results of the analysis obtained at a given time undergoing the subsequent processing in the microprocessor 8 and being transmitted to the module 2 while a new analysis is undertaken at 9 in the succeeding analysis window.

Certainly, this manner of working introduces a delay into the transmission of the elements of the sound spectrum to the auditory nerve of the patient, but this delay remains substantially constant and small and is not therefore able to disturb the conduct of a conversation. The delay may be of the order of a few tenths of a second at most, this being comparable with the delays which may be encountered in some long-distance satellite telephone links.

The frequency cue If and time cue It are next subjected at 10 to a so-called processing of the "stationarities" enabling the ambient noise of the sound spectrum to be identified and possibly eliminated from the cue transmitted.

This identification may possibly be facilitated by providing an auxiliary microphone (not represented) whose signals, after digitization, are applied to the microprocessor 8, the link being symbolized in FIG. 2 by the dashes 11. Furthermore, the implementation of this function may be made adjustable in such a way that the patient can himself control the application thereof to the cue transmitted to the ear and thus possibly improve the signal/noise ratio by eliminating the frequencies belonging to the ambient noise.

The means symbolized by the rectangle 12 implement the application of the data of the general model of the inner ear based on a subject with normal hearing, to the frequency cue and time cue formulated by applying the functions 9 and 10. These data correspond to the result of an instantaneous transcoding between the sound levels corresponding to each of the frequency bands analyzed and the electrical pulses theoretically measurable at the corresponding sites of the cochlea of an individual with normal hearing. Thus, by virtue of the invention, this model can take into account not only the tonotopy of the cochlea, that is to say the correspondence between various points of the cochlea and the various frequencies constituting the range of audible sounds, but also the temporal behavior of the cochlea, that is to say for example the time offsets encountered in the transmission over the auditory nerve of a normal hearer of the various instantaneous frequency components of a sound signal, in particular of short duration.

The function symbolized by the rectangle 13 represents the application of analog data relating to the personalized model of the implanted electrodes which it may be possible to observe in the patient wearing the hearing aid.

It should be noted that the means 12 and 13 may be implemented for example by storing equivalence tables in the memory of the microprocessor, enabling corrections of amplitude, frequency and occurrence in time to be assigned to the instantaneous data relating to each elementary frequency band.

Control means 14 also embodied by the microprocessor 8 are intended to shape the frequency and time cues, possibly corrected by the parameters formulated by the means 12 and 13, so that these cues may be transmitted to the electrodes e1, e2, ... en arranged within the tympanic lip of the patient. These control means thus make it possible to construct, for each electrode, an energy signal which groups together the cues relating to energy, recurrence and synchronization, this last cue representing the temporal ratio between the signal relating to a given electrode and those of the other electrodes.

The control means 14 of the outer module 1 may be designed essentially according to two modes of implementation.

They may generate a repetitive pulse train intended to be applied in the form of a cyclic frame to the electrodes e1 to en via the transmitter 3, and the units of the implantable module 2, that is to say the receiver 4 and the control circuit 15. The latter also provides the electrical power supply to the electrodes and possibly to the other circuits of the inner module 2, employing the energy transmitted through the transmitter 3 and the receiver 4.

Each frame then comprises a cue relating to the ratio between the frequency of recurrence of the pulse on the relevant electrode and the frequency of the transmission frame. The frame may also comprise a cue relating to the gap in synchronism between the relevant pulse and a time reference, it being possible for the latter to be identical for all the electrodes. For example, the time reference may be the start of the first pulse of each frame.

These various cues may be transmitted by combining various modulations of the transmitted signal, for example by amplitude, frequency and/or phase modulation.

The other mode of implementation may consist in generating a succession of binary words each containing the order number of the electrode, the amplitude of the pulse to be applied, the frequency of recurrence of the pulses for each electrode and/or the synchronization gap with respect to the reference.

The control circuit 15 located in the implantable module 2 is designed to decode all of the cues reaching it through the transmitter 3 and the receiver 4. It therefore produces the sequences for operating the electrodes in accordance with the commands which reach it via the control means 15.

FIGS. 3a to 3c illustrate the operation of the hearing aid according to the invention in the case in which the electrodes receive their control pulses through frequency modulation of a carrier wave transmitted from the transmitter 3 to the receiver 4. To simplify these figures it has been assumed that the hearing aid has only five pairs of electrodes e1 to e5. Furthermore, the example refers to the perception of the word "ALICE" uttered by a French speaker and for which FIG. 1a shows the waveform issuing from the microphone 6, as a function of time t. The chart of FIG. 1b shows its analysis by wavelet transform carried out on a large number of sampling points and over 57 channels, with the help of time windows varying with frequency. The chart of FIG. 1b demonstrates very clearly the energy content of the various frequency bands (here the frequency is plotted as ordinate). For example, the vowel "A" at the start of the utterance of the word, shows a succession of "black spots" which are due to this vowel.

As already indicated, it is assumed that the hearing aid comprises five electrodes respectively assigned to five corresponding frequency bands. The chart of FIG. 3a represents the distribution of these frequency bands among the electrodes e1 to e5, the highest-frequency band being assigned to electrode e1 and the lowest-frequency band to electrode e5.

It will furthermore be observed that in order to reconstruct the word "ALICE", the bottom two frequency bands are considered not to contain any telltale cue and it is considered unnecessary to transmit this cue to the electrodes e4 and e5. Consequently, in FIG. 3b, the lines corresponding to the electrodes e4 and e5 are void.

FIG. 3b therefore shows merely the signals corresponding to the significant electrodes e1, e2 and e3. Moreover, represented symbolically in the line labelled "tr" is the synchronization of the frames in which the cues destined for the electrodes are transmitted to the latter. For the purpose of the representation, each frame is thus symbolized by a single bar.

At the start of the example, if the first information cue x1 is considered, it is seen that three frames tr1 are required in order to transcribe it, the first frame being synchronized with the start of x1. These frames are uniformly spaced in time (time T) and still only relate to the electrode e2. The second information cue x2 includes a fragment for the electrode e1 and a fragment for the electrode e2. This cue can be transcribed by four frames tr1 uniformly spaced and synchronized with the start of the cue x2. Transcription is continued thus via frames tr1 until the information becomes less dense. It will be noted that just before the end of this phase (cue x3), the three electrodes e1, e2 and e3 are all involved.

Onwards of the cue x4, the density of the information to be transmitted decreases. It may then be satisfactory to space out the frames (henceforth labelled tr2), the start of each frame or group of frames remaining synchronized with the appearance of the information cue of the relevant electrode.

The frames tr3 correspond alternately to cues assigned to the electrodes e1 and e3. They therefore appear along with the appearance of these cues and are synchronized with them.

The information cues x5 also relate to two electrodes e1 and e3, but in this case they are spaced apart by a duration smaller than that of a frame.

However, these frames tr4 have this in particular that the cue assigned to the electrode e1 appears later than that of the electrode e3. This time relation, taken into account by virtue of the invention and in particular of the procedure of analysis using a wavelet transform, can be used to control the relevant electrodes.

This is represented, on an enlarged time scale, in FIG. 3c which shows the conduct of the control procedure for these electrodes. This chart depicts firstly the last frame tr4 of FIG. 3b. It can be seen that the frame begins with a synchronization pulse Is followed by five pulses relating respectively to the electrodes e1 to e5. It will be noted that each frame always includes one electrode cue for each of them so as to be able to temporally locate the useful cue relating to each electrode. Thus in the frame represented, the cue relating to electrode e1 is significant and corresponds to a pulse whose width evidences the energy required to be transmitted to this electrode. On the other hand, the electrode e2 is not involved during this frame, which therefore contains only a short command pulse relating to this electrode. Next, the cue destined for the electrode e3 is likewise represented by an energy pulse, whereas the electrodes e4 and e5 are represented only by their command pulse.

It will be understood that each frame (whether it be this specific frame tr4 or the other frames tr1, tr2 or tr3) is thus transmitted between the transmitter 3 and the receiver 4 accompanied by a phase cue which represents the required time relation between the pulses destined respectively for electrodes e1 and e3 (offset Td and order of appearance).

Thus in the example of FIG. 3c, the electrodes e1 to en are operated with a certain delay, depending on the computation time required by the microprocessor, with respect to the start of the relevant frame. According to the command cue (not represented) mentioned above, associated with frame tr4, the electrode e3 is to be excited before the electrode e1. The electrode e3 is therefore excited first and the electrode e1 is excited with the abovementioned delay Td with respect to the electrode e3.

The transmission is carried out, for example by means of a carrier, the on/off amplitude modulation of which corresponds to the energy pulses and can be frequency or phase modulated for example as regards the time relation between the cues destined for the various electrodes. The decoding of such a modulated carrier is undertaken in the control circuit 15 incorporated into the inner module 2.

It will be understood that transmission of the cues to this circuit and decoding are carried out with a very slight time gap relative to the production of the contents of each frame, as may be seen elsewhere in FIG. 3c. However, the preparation of a given frame may be carried out while the previously prepared frame is transmitted and decoded so that the perception of the sound spectrum undergoes no discontinuity.

I claim:

1. A hearing aid comprising:

n electrodes for being implanted in a cochlea at n different points chosen to allow identification by a brain of a plurality of different frequency bands of a sound spectrum;

a microphone for receiving the sound spectrum and outputting a sound signal representing the sound spectrum;

energy measuring means for measuring an instantaneous energy of the sound signal in said frequency bands;

electrode operating means for cyclically operating said n electrodes as a function of the instantaneous energy measured in the respective frequency bands;

time distribution determining means for determining a time distribution within the sound signal of the instantaneous energy in each of said frequency bands; and electrode exciting means for exciting said electrodes at each cycle in an order corresponding to said time distribution.

2. The hearing aid as claimed in claim 1, wherein said time distribution determining means comprises means for applying a wavelet transform to said sound signal.

3. The hearing aid as claimed in claim 2, wherein said electrode exciting means comprises means for producing trains of successive pulses constituting a frame in which said pulses are defined as a function of said instantaneous energy and of said time distribution.

4. The hearing aid as claimed in claim 3, wherein said electrode exciting means further comprises means for defining said pulses by at least one of their duration, their frequency of recurrence and their relative phase.

5. The hearing aid as claimed in claim 4, wherein said time distribution is defined with respect to a time reference.

6. The hearing aid as claimed in claim 5, wherein said time reference is a start of a first pulse of each of the frames.

7. The hearing aid as claimed in claim 2, wherein said electrode exciting means comprises means for producing a succession of binary words comprising command cues for operating said electrodes, the command cues indicating at least one of an amplitude of pulses to be applied to the electrodes and an energy required to be contained in said pulses.

8. The hearing aid as claimed in claim 1, wherein said electrode exciting means comprises means for producing trains of successive pulses constituting a frame in which said pulses are defined as a function of said instantaneous energy and of said time distribution.

9. The hearing aid as claimed in claim 8, wherein said electrode exciting means further comprises means for defining said pulses by at least one of their duration, their frequency of recurrence and their relative phase.

10. The hearing aid as claimed in claim 9, wherein said time distribution is defined with respect to a time reference.

11. The hearing aid as claimed in claim 10, wherein said time reference is a start of a first pulse of each of the frames.

12. The hearing aid as claimed in claim 1, wherein said electrode exciting means comprises means for producing a succession of binary words comprising command cues for operating said electrodes, the command cues indicating at least one of an amplitude of pulses to be applied to the electrodes and an energy required to be contained in said pulses.

13. The hearing aid as claimed in claim 1, further comprising ear modeling means for controlling the electrode exciting means to excite the electrodes in accordance with at least one of a physiological behavior of an ear of a normal hearer and a behavior of the electrodes.

14. The hearing aid as claimed in claim 1, further comprising stationarity processing means for controlling the electrode exciting means to excite the electrodes in accordance with an ambient noise.

* * * * *